United States Patent [19]

Fischer et al.

[11] Patent Number: 4,529,814

[45] Date of Patent: Jul. 16, 1985

[54] ACYLOXYALKADIENOATES AND THEIR PREPARATION

[75] Inventors: Rolf Fischer, Heidelberg; Hans-Martin Weitz, Bad Durkheim, both of Fed. Rep. of Germany

[73] Assignee: BASF Aktiengesellschaft, Fed. Rep. of Germany

[21] Appl. No.: 419,490

[22] Filed: Sep. 17, 1982

[30] Foreign Application Priority Data

Sep. 23, 1981 [DE] Fed. Rep. of Germany ....... 3137801

[51] Int. Cl.$^3$ .............................................. C07C 69/73
[52] U.S. Cl. .................................. 560/183; 560/181; 260/410.9 R
[58] Field of Search ..................... 560/183, 185, 181; 562/579; 260/410.9 M

[56] References Cited

U.S. PATENT DOCUMENTS 2,466,738  4/1949  Phillips ................................. 260/549
3,161,672  12/1964  Zachry et al. ......................... 560/207

FOREIGN PATENT DOCUMENTS 2820519  11/1979  Fed. Rep. of Germany .
2943407   5/1981  Fed. Rep. of Germany .

OTHER PUBLICATIONS

Funakoshi, Wataru et al., Chemical Abstracts, vol. 84, (1976), #43,356x, (Japanese Kokai 75-130,714).
Fueno, Takayuki et al., J. Am. Chem. Society, vol. 94, (1972), pp. 1119–1125.
DePuy, C. H. et al., J. Am. Chem. Society, vol. 96, (1974), pp. 5602–5604.
Takaiwa, Akihiro et al., Agricultural & Biological Chemistry, (vol. 46), Jun. 1982, pp. 1721–1722.
Hackh's Chemical Dictionary, 4th Ed. McGraw-Hill, publ. p. 625.

Primary Examiner—Natalie Trousof
Assistant Examiner—L. Hendriksen
Attorney, Agent, or Firm—Keil & Weinkauf

[57] ABSTRACT

Acyloxyalkadienoates of the formula

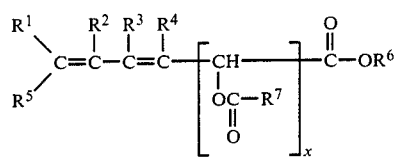

where $R^1$, $R^2$, $R^3$, $R^6$ and $R^7$ are each hydrogen or a hydrocarbon radical, and $R^1$ may furthermore be $R^6$—O—CO—, $R^4$ is hydrogen or a hydrocarbon radical, but may only be hydrogen if x is 0, $R^5$ is hydrogen, or is

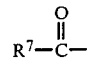

if x is 0, and x is 0 or 1, and their preparation.

3 Claims, No Drawings

ACYLOXYALKADIENOATES AND THEIR PREPARATION

The present invention relates to novel acyloxyalkadienoates and to a process for their preparation.

The novel acyloxyalkadienoates are of the general formula

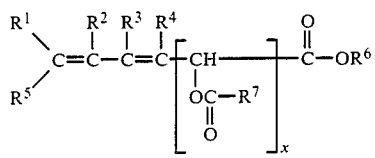

where $R^1$ is hydrogen, a hydrocarbon radical of 1 to 5 carbon atoms or $R^6$—O—CO—, $R^2$ and $R^3$ are each hydrogen or a hydrocarbon radical of 1 to 5 carbon atoms, $R^4$ is hydrogen or a hydrocarbon radical of 1 to 5 carbon atoms, but must be hydrogen if x is O, $R^5$ is hydrogen, or is

if x is O, $R^6$ is a hydrocarbon radical of 1 to 15 carbon atoms, $R^7$ is hydrogen or a hydrocarbon radical of 1 to 5 carbon atoms and x is O or 1.

Examples of hydrocarbon radicals in the compounds of the formula I are alkyl, alkenyl, and alkadienyl radicals, eg. $CH_3$—, $C_2H_5$—, $C_3H_7$—, n-$C_4H_9$—, sec.-butyl-, i-butyl-, tert.-butyl, $CH_2$=CH—, $CH_3$—CH=CH—, $CH_2$=CH—CH=CH—$CH_2$—, n-$C_5H_{11}$—, n-$C_{10}H_{21}$—, n-$C_{12}H_{25}$— or n-$C_{15}H_{31}$—. Hydrocarbon radicals of not more than 15 carbon atoms may also be cycloalkyl, aryl or benzyl.

Of particular industrial interest are those compounds of the formula I where $R^1$, $R^2$, $R^3$, $R^4$, $R^6$ and $R^7$ are each hydrogen or alkyl of 1 to 3 carbon atoms.

The novel acyloxyalkadienoates of the formula I are prepared by a process in which a diene of the formula

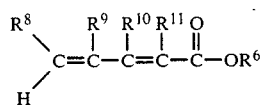

where $R^8$ is hydrogen, a hydrocarbon radical of 1 to 5 carbon atoms or $R^6$—O—CO—, and $R^9$, $R^{10}$ and $R^{11}$ are each hydrogen or a hydrocarbon radical of 1 to 5 carbon atoms, is treated with a carboxylic acid of the formula $R^7COOH$, in the presence of a catalyst containing palladium or platinum or a salt of one of these metals, and of oxygen.

Where methyl sorbate (methyl 2,4-hexadienoate) is reacted with acetic acid and oxygen, the reaction may be represented by the following equation (OAc =

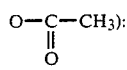

):

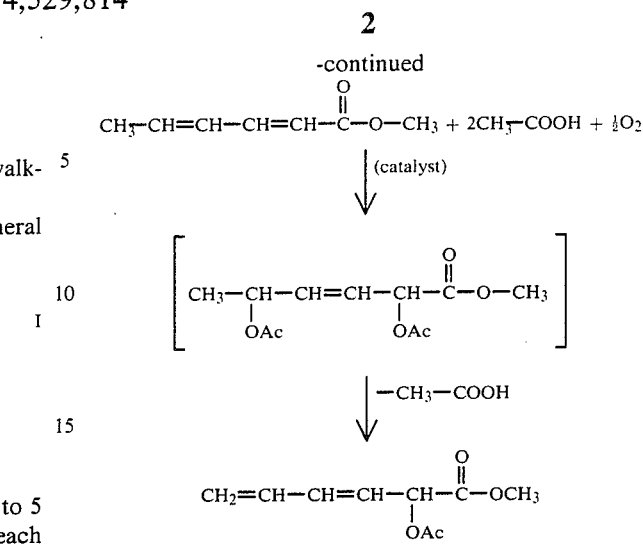

It has been disclosed that 1-acetoxy-1,3-butadiene can be reacted with acetic acid and oxygen in the presence of a catalyst containing palladium and one or more additional elements to give a 1,1,4-triacetoxybut-2-ene (German Pat. No. 2,819,592 and German Laid-Open Application DOS No. 2,842,238).

It has also been disclosed that when 1-acetoxy-1,3-butadiene is reacted with acetic acid and oxygen in the presence of a catalyst containing palladium and an alkali metal salt of a carboxylic acid a mixture of 1,4-diacetoxybut-2-ene and 3,4-diacetoxybut-1-ene is formed (German Laid-Open Application DOS No. 2,200,124). Thus, in this reaction, only one molecule of acetic acid undergoes adduct formation at the double bond of the 1,3-diene.

Although acyloxy groups

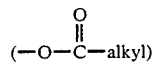

and alkoxycarbonyl groups

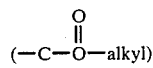

are structurally isomeric groups, they differ from one another substantially in respect of chemical behaviour. Thus, it was not possible to predict the behaviour of an acyloxyalkadienoate when reacted with oxygen and a carboxylic acid. By analogy with the reaction of 1-acetoxy-1,3-butadiene with acetic acid and oxygen, it was to be expected that, for example when methyl sorbate was treated with acetic acid and oxygen, methyl 2,5-diacetoxyhex-3-enecarboxylate or methyl 5-acetoxyhex-3-enecarboxylate, rather than methyl 2-acetoxy-3,5-hexadienoate, would be formed. The fact that the reaction according to the invention would lead predominantly to 1,3-diene derivatives could not be foreseen. The process of the present invention gives the novel acyloxyacyloxyalkadienoates in a particularly advantageous, one-stage reaction.

Examples of starting materials of the formula II are the methyl, ethyl, propyl, butyl, pentyl, cyclopentyl, cyclohexyl, benzyl and phenyl esters of 2,4-pentadienecarboxylic acid, 3-methyl-2,4-pentadienecarboxylic acid, 4-methyl-2,4-pentadienecarboxylic acid, 3-n-propyl-2,4-pentadienecarboxylic acid, 4-tert.-butyl-2,4-pentadienecarboxylic acid, 3,4-dimethyl-2,4-pentadienecarboxylic acid, 3,4-di-n-butyl-2,4-pentadienecarboxylic acid, 4-(but-2-enyl)-2,4-pentadienecarboxylic acid, 3-(pent-2-enyl)-2,4-pentadienecarboxylic acid, 2,4-hexadienecarboxylic acid, 2,4-heptadienecarboxylic acid, 2,4-octadienecarboxylic acid, 2,4-nonadienecarboxylic acid, 3-methyl-2,4-hexadienecarboxylic acid, 4-ethyl-2,4-heptadienecarboxylic acid, 2,4-hexadienecarboxylic acid, 3-methyl-2,4-hexadienedicarboxylic acid and 3,4-dimethyl-2,4-hexadienedicarboxylic acid.

The above starting compounds II can be prepared in a conventional manner (Houben-Weyl, Methoden der organischen Chemie, 4th Edition, Volume V/1c, pages 1 to 853). Thus, methyl sorbate is obtainable, for example, from crotonaldehyde and ketene or malonic acid, and methyl 2,4-pentadienoate is obtainable, for example, by splitting off two molecules of hydrogen bromide from methyl 3,4-dibromopentanecarboxylate.

Examples of suitable carboxylic acids of the formula $R^7COOH$ are formic acid, acetic acid, propionic acid, butyric acids and valeric acids.

The catalysts used are palladium or platinum, or salts of these metals, and may contain other active constituents. Examples of suitable catalysts are supported catalysts which contain, as active constituents applied onto the carrier, palladium or platinum and copper and/or tellurium. The catalysts may be prepared in a conventional manner, for example as described in German Pat. No. 2,217,452 and German Laid-Open Applications DOS No. 2,943,407, DOS No. 2,820,519, DOS No. 2,417,452, DOS No. 2,820,519 or DOS No. 2,417,558. Catalysts of the above type contain, for example, from 1 to 10% of palladium or platinum, from 0.1 to 30% of copper and/or from 0.01 to 10% of tellurium, the percentages being based on the weight of the catayst. It is preferable to use a supported catalyst which contains, per gram atom of palladium or platinum, from 0.01 to 6, preferably from 1 to 3.5, gram atoms of copper and/or from 0.01 to 1, preferably from 0.01 to 0.4, gram atom of tellurium. The total amount of catalytically active metals applied onto the carrier is advantageously, for example, from 0.01 to 30% by weight, based on the supported catalyst. However, larger or smaller amounts may also be used. The carrier material of the catalysts is, for example, active charcoal, bauxite, pumice, silica gel, kieselguhr or some other form of silica, magnesium oxide, or aluminum oxide.

The catalytically active metals can, for example, also be employed in the absence of a carrier, by using metal salts and dissolving or suspending these in the reaction mixture.

In the preparation of the compounds of the formula I, the reaction is carried out in a conventional manner, either in the gas phase or in the liquid phase, at from 70° to 180° C. When working in the gas phase the reaction temperature is preferably from 120° to 150° C., and when working in the liquid phase the corresponding temperature is preferably from 70° to 110° C. The reaction pressure depends on the procedure and may be from atmospheric pressure to, for example, 100 bar. The process may be carried out batchwise or continuously, for example using a fixed bed, fluidized bed or three-phase fluidized bed. When the reaction is complete, any reacted compound of the formula II and the particular carboxylic acid used can be distilled from the reaction mixture and may be reused, for example in the form of this mixture.

The novel acyloxyalkadienoates are useful intermediates. Thus, for example, they can undergo Diels-Alder reactions with dienophiles to give cyclohexene derivatives which are substituted by alkyl, acetoxy or alkoxycarbonyl groups. Splitting off acetic acid and/or hydrogen gives a large variety of benzene, phenol and benzoic acid derivatives which are useful in the preparation of dye intermediates, dyes and drugs. Thus, when methyl 2-acetoxy-3,5-hexadienoate is reacted with ethylene and the product dehydrogenated, a mandelic acid derivative is obtained; this derivative gives mandelic acid on hydrolysis, or cinnamic acid when acetic acid is split off. For example, methyl benzoate can be prepared by reacting methyl 5-acetoxy-2,4-pentadienoate with ethylene, splitting off acetic acid from the cyclohexene derivative formed, and then dehydrogenating this product.

EXAMPLE 1

600 g of glacial acetic acid and 25 g of a supported Pd/Cu/Te catalyst (5.1% of Pd, 8.5% of Cu and 0.9% of Te on active charcoal) prepared as described in German Laid-Open Application DOS No. 2,943,407 are introduced into a 1 liter three-necked flask equipped with an Anschütz head, a dropping funnel, a gassing stirrer, an internal thermometer, a gas inlet tube and a reflux condenser surmounted by a dry-ice condenser, after the apparatus has been flushed with nitrogen. The mixture is heated to 95° C. In the course of 4 hours, while stirring, 12 liters of oxygen are passed in and at the same time 63 g of methyl sorbate are added dropwise. After the addition is complete, 1.5 liters of oxygen are passed through the reaction mixture at 95° C. in the course of 30 minutes, after which nitrogen is passed through. The mixture is cooled and the catalyst is filtered off. Fractional distillation of the filtrate gives, in addition to unreacted methyl sorbate, 21 g of methyl 2-acetoxy-3,5-hexadienoate of boiling point 88°–115° C./25 mbar and $n_D^{20} = 1.4922$.

The catalyst is prepared by mixing Cu powder dissolved in 33% strength nitric acid with a solution of $PdCl_2$ in a warm 1:1 (by volume) mixture of 66% strength nitric acid and 32% strength hydrochloric acid and with a solution of $TiO_2$ in warm 16% strength hydrochloric acid. The combined metal salt solution is added to 100 g of active charcoal (0.3–0.5 mm), which has beforehand been stirred for 5 hours with 15% strength nitric acid at 70° C., and then been filtered off, washed neutral and dried under reduced pressure at 150° C. (sulfur content of the charcoal 0.21%). Sufficient water is then added to the charcoal/metal salt solution mixture that the charcoal is fully wetted. The mixture is then evaporated to dryness on a rotary evaporator at 85° C. under reduced pressure from a water-pump. Thereafter the catalyst is dried for 2 hours at 150° C. in a drying oven under reduced pressure, followed by 2 hours at 150° C. in a tubular furnace under a stream of nitrogen. It is then activated with nitrogen, which has been saturated with methanol at room temperature, for 6 hours at 200° C. followed by 6 hours at 400° C., and finally with hydrogen (20 liters/hour) at 800° C. for half an hour. The catalyst is then allowed to cool to room temperature under a stream of nitrogen.

EXAMPLE 2

56 g of methyl 2,4-pentadienoate are suspended in 543 g of glacial acetic acid in the presence of 50 g of a Pd/Cu catalyst (5% of Pd and 9.2% of Cu) prepared as described in German Laid-Open Application DOS No. 2,820,519, and reacted with 12 liters of oxygen at 95° C. in the course of 4 hours, all as described in Example 1. The mixture is worked up as described in Example 1 and then fractionally distilled, giving, in addition to unreacted methyl 2,4-pentadienoate, 13 g of methyl 2,5-diacetoxypent-3-enecarboxylate of boiling point 113°–115° C./0.4 mbar ($n_D^{20}=1.4600$) and 19.5 g of methyl 5-acetoxy-2,4-pentadienoate of boiling point 125°–131° C./13 mbar and melting point 54°–56° C. (from methanol).

The catalyst is prepared by mixing $PdCl_2$ dissolved in a mixture of 20 ml of 4N hydrochloric acid, 20 ml of 30% strength nitric acid and a solution of copper powder in 84 ml of 30% strength nitric acid. 100 g of active charcoal of particle size 0.4–0.8 mm, which has been washed with nitric acid, are moistened with 100 ml of water, the solution is added and the mixture is boiled. Whilst it is boiling, a solution of 70 g of hydrazine hydrochloride, 400 ml of water and 300 ml of aqueous 15% strength ammonia solution is added gradually and the mixture is stirred for a further 1.5 hours at the boil. The suspension is filtered and the residue is washed neutral with water, rinsed with 50 ml of methanol, dried for 10 hours under reduced pressure at 70° C. and treated for 30 minutes at 800° C. with hydrogen in a tubular furnace.

We claim:

1. An acyloxyalkadienoate of the formula

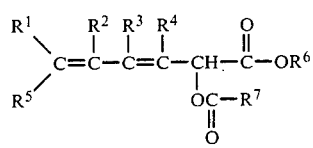

where $R^1$ is hydrogen, a hydrocarbon radical of 1 to 5 carbon atoms or $R^6$—O—CO—, $R^2$, $R^3$, $R^4$ and $R^7$ are each hydrogen or a hydrocarbon radical of 1 to 5 carbon atoms, $R^5$ is hydrogen and $R^6$ is a hydrocarbon radical of 1 to 15 carbon atoms.

2. An acyloxyalkadienoate as defined in claim 1 wherein $R^1$, $R^2$, $R^3$, $R^4$, $R^6$, and $R^7$ are hydrogen or alkyl of 1 to 3 carbon atoms.

3. Methyl 2-acetoxy-3,5-hexadienoate.

* * * * *